(12) United States Patent
Bell et al.

(10) Patent No.: US 9,428,627 B2
(45) Date of Patent: Aug. 30, 2016

(54) MANUFACTURE OF DIHYDROXY AROMATIC COMPOUNDS BY ALCOHOLYSIS OF FLAME RETARDANT-CONTAINING POLYCARBONATE COMPOSITIONS

(71) Applicant: SABIC Global Technologies B.V., Bergen op Zoom (NL)

(72) Inventors: Philip Wesley Bell, Mount Vernon, IN (US); Vic Ignacio Fernandez, Murcia (ES); Venkata Ramanarayanan Ganapathy Bhotla, Karnataka (IN); Tukaram Gunale, Bangalore (IN); Alexander Stanislaus, Bangalore (IN); Darshan Jayanna, Tumkur (IN)

(73) Assignee: SABIC GLOBAL TECHNOLOGIES B.V. (NL)

( * ) Notice: Subject to any disclaimer, the term of this patent is extended or adjusted under 35 U.S.C. 154(b) by 0 days.

(21) Appl. No.: 14/440,162

(22) PCT Filed: Dec. 11, 2013

(86) PCT No.: PCT/US2013/074403
§ 371 (c)(1),
(2) Date: May 1, 2015

(87) PCT Pub. No.: WO2014/099550
PCT Pub. Date: Jun. 26, 2014

(65) Prior Publication Data
US 2015/0291763 A1    Oct. 15, 2015

(30) Foreign Application Priority Data
Dec. 21, 2012 (EP) .................................... 12382521

(51) Int. Cl.
| | |
|---|---|
| *C08G 64/00* | (2006.01) |
| *C08J 11/24* | (2006.01) |
| *C07C 68/06* | (2006.01) |
| *C08G 64/30* | (2006.01) |
| *C08L 69/00* | (2006.01) |
| *C07C 37/055* | (2006.01) |
| *C08G 63/02* | (2006.01) |

(52) U.S. Cl.
CPC ............ *C08J 11/24* (2013.01); *C07C 37/0555* (2013.01); *C07C 68/06* (2013.01); *C08G 64/307* (2013.01); *C08L 69/00* (2013.01); *C08J 2369/00* (2013.01); *Y02W 30/706* (2015.05)

(58) Field of Classification Search
CPC ................. C08J 11/24; C07C 68/07
USPC ............ 528/196, 198, 271, 272, 273, 274; 524/480, 502, 611; 521/48.5
See application file for complete search history.

(56) References Cited

U.S. PATENT DOCUMENTS

| | | | |
|---|---|---|---|
| 4,154,775 A | 5/1979 | Axelrod | |
| 4,447,659 A | 5/1984 | Blewett | |
| 5,045,122 A | 9/1991 | Tindall et al. | |
| 5,266,716 A * | 11/1993 | Buysch | ................. C07C 68/06 558/260 |
| 5,350,839 A | 9/1994 | Asaka et al. | |
| 5,391,802 A | 2/1995 | Buysch et al. | |
| 5,440,066 A | 8/1995 | Buysch et al. | |
| 6,787,632 B2 | 9/2004 | Phelps et al. | |
| 6,887,968 B2 | 5/2005 | Hahnsen et al. | |
| 7,094,917 B2 | 8/2006 | Ridinger et al. | |
| 7,585,930 B2 | 9/2009 | Kitahara et al. | |
| 8,680,226 B1 * | 3/2014 | Bell | ..................... C08J 11/24 524/480 |
| 8,846,858 B2 * | 9/2014 | Bell | ..................... C07C 37/84 524/480 |
| 2004/0054238 A1 * | 3/2004 | Ban | ..................... C07C 68/06 568/723 |
| 2004/0127720 A1 * | 7/2004 | Hedrick | ............ C07C 59/285 548/530 |

FOREIGN PATENT DOCUMENTS

| | | |
|---|---|---|
| EP | 1439158 A1 | 7/2004 |
| EP | 2746249 A1 | 6/2014 |
| GB | 2043083 A | 10/1980 |
| JP | H03291257 A | 12/1991 |
| JP | H04211038 A | 8/1992 |
| JP | 2001302844 A | 10/2001 |
| JP | 2006088334 A | 4/2006 |
| JP | 2008189766 A | 8/2008 |
| JP | 20100222556 A | 10/2010 |
| JP | 2015533816 A | 11/2015 |
| WO | 2009066616 A1 | 5/2009 |

OTHER PUBLICATIONS

Anonymous; "Polycarbonate Recycling"; Research Disclosure; Sep. 1997; 2 pages.
DE 4324778, Publication date: Jan. 26, 1995, Abstract, 1 page.
DE 4326906 (C1), Publication date: Feb. 16, 1995, Abstract, 1 page.
European Search Report for International Application No. 12382521.8; Date of Completion May 14, 2013; 6 pages.
JP2001302844 A English Abstract; Date of Publication Oct. 31, 2001; 2 pages.
JP2003041049 A English Abstract; Date of Publication Feb. 13, 2003; 1 page.
JP2005343840 A English Abstract; Date of Publication Dec. 15, 2005; 2 pages.
Patent Cooperation Treaty, International Searching Authority, PCT/US2013/074617, Written Opinion, Date of mailing: Feb. 13, 2014, 5 pages.

(Continued)

*Primary Examiner* — Terressa Boykin
(74) *Attorney, Agent, or Firm* — Cantor Colburn LLP

(57) ABSTRACT

The disclosure provides a method for recovering a dihydroxy aromatic compound and a dialkyl carbonate from a polycarbonate-containing composition comprising a polycarbonate and a phosphorus-containing flame retardant. The method comprises heating the composition in the presence of an alcohol and a transesterification catalyst having non-neutralizable groups at a temperature of 70° C. to 200° C. and a pressure of 50 mbar to 40 bar for a time sufficient to depolymerize the polycarbonate producing a dihydroxy aromatic compound and a dialkyl carbonate.

20 Claims, No Drawings

(56) References Cited

OTHER PUBLICATIONS

Patent Cooperation Treaty, International Searching Authority, Search Report, PCT/US2013/074400, Date of mailing: Feb. 17, 2014, 4 pages.
Patent Cooperation Treaty, International Searching Authority, Search Report, PCT/US2013/074403, Date of mailing: Feb. 18, 2014, 5 pages.
Patent Cooperation Treaty, International Searching Authority, Search Report, PCT/US2013/074617, Date of mailing: Feb. 13, 2014, 4 pages.
Patent Cooperation Treaty, International Searching Authority, Written Opinion, PCT/US2013/074400, Date of mailing: Feb. 17, 2014, 4 pages.
Patent Cooperation Treaty, International Searching Authority, Written Opinion, PCT/US2013/074403, Date of mailing: Feb. 18, 2014, 7 pages.

* cited by examiner

MANUFACTURE OF DIHYDROXY AROMATIC COMPOUNDS BY ALCOHOLYSIS OF FLAME RETARDANT-CONTAINING POLYCARBONATE COMPOSITIONS

This application is a National Stage filing under 371 of PCT Application No. PCT/US13/74403, filed Dec. 12, 2013, which claims Priority to European Application No. EP12382521.8, filed on Dec. 21, 2012.

BACKGROUND

This disclosure is directed to methods for the manufacture of dihydroxy aromatic compounds and dialkyl carbonates from flame retardant-containing polycarbonate compositions, and in particular to methods of making bisphenol A and dimethyl carbonate by methanolysis of bisphenol A polycarbonate composition containing phosphorus-containing flame retardants.

Polycarbonates are useful in the manufacture of articles and components for a wide range of applications, from automotive parts to electronic appliances. However, polycarbonates are not biodegradable and can present a significant bulk waste disposal problem. Accordingly, efforts have been made to recover valuable resources from polycarbonate wastes.

Polycarbonates can depolymerize in the presence of a catalyst to generate monomers such as bisphenol A and dimethyl carbonate. However, it is challenging to depolymerize polycarbonates in wastes, particularly, post-consumer low purity wastes, since these wastes contain various chemicals in addition to polycarbonates. These various chemicals can poison the catalyst, contaminate the products, and render the process expensive and inefficient. Thus, a cost effective process that allows the recovery of high quality products from polycarbonate wastes is continuously sought.

BRIEF DESCRIPTION

The disclosure provides a method for recovering a dihydroxy aromatic compound and a dialkyl carbonate from a polycarbonate-containing composition comprising a polycarbonate and a phosphorus-containing flame retardant. The method comprises heating the polycarbonate-containing composition in the presence of an alcohol and a transesterification catalyst having non-neutralizable groups at a temperature of 70° C. to 200° C. and a pressure of 50 mbar to 40 bar for a time sufficient to depolymerize the polycarbonate to provide a dihydroxy aromatic compound and a dialkyl carbonate.

The disclosure also provides a method for the manufacture of a polycarbonate. The method comprises heating a polycarbonate-containing composition in the presence of an alcohol and a transesterification catalyst having non-neutralizable groups at a temperature of 70° C. to 200° C. and a pressure of 50 mbar to 40 bar for a time sufficient to depolymerize the polycarbonate to provide a dihydroxy aromatic compound and a dialkyl carbonate, the polycarbonate-containing composition comprising a polycarbonate and a phosphorus-containing flame retardant; recovering the dihydroxy aromatic compound; and polymerizing the dihydroxy aromatic compound and a carbonyl source to provide the polycarbonate. A polycarbonate manufactured by the method is also provided.

A method to manufacture diphenyl carbonate is also provided. The method comprises heating a polycarbonate-containing composition in the presence of an alcohol and a transesterification catalyst having non-neutralizable groups at a temperature of 70° C. to 200° C. and a pressure of 50 mbar to 40 bar for a time sufficient to depolymerize the polycarbonate to provide a dihydroxy aromatic compound and a dialkyl carbonate, the polycarbonate-containing composition comprising a polycarbonate and a phosphorus-containing flame retardant; recovering the dialkyl carbonate; and reacting the dialkyl carbonate with phenol to provide diphenyl carbonate.

An alternative method for the manufacture of a polycarbonate comprises: heating a polycarbonate-containing composition in the presence of an alcohol and a transesterification catalyst having non-neutralizable groups at a temperature of 70° C. to 200° C. and a pressure of 50 mbar to 40 bar for a time sufficient to depolymerize the polycarbonate and produce a dihydroxy aromatic compound and a dialkyl carbonate, the polycarbonate-containing composition comprising a polycarbonate and a phosphorus-containing flame retardant; recovering the dihydroxy aromatic compound and the dialkyl carbonate; reacting the dialkyl carbonate with phenol to provide diphenyl carbonate; polymerizing the dihydroxy aromatic compound and diphenyl carbonate to provide the polycarbonate. The disclosure also provides a polycarbonate manufactured by the method.

These and other non-limiting characteristics are more particularly described below.

DETAILED DESCRIPTION

Polycarbonates can be depolymerized using a base catalyst. However, the inventors found that when a base catalyst is used with polycarbonates containing phosphorus-containing flame retardants, the depolymerization of the polycarbonates is incomplete unless large amounts of catalyst are used. For example, for sodium hydroxide, 1.25% catalyst loading was ineffective while 2.5% catalyst loading resulted in complete conversion. For potassium hydroxide, 2.5% catalyst loading was ineffective while 5% catalyst loading resulted in complete conversion. For triethylamine, 0.75% catalyst loading was ineffective while 1.25% catalyst loading resulted in complete conversion. Surprisingly, the use of a transesterification catalyst having non-neutralizable groups, for example tetra(isopropyl)titanate, aluminum isopropoxide and dibutyltin oxide, allows for complete depolymerization of the polycarbonate in the presence of a phosphorus-containing flame retardant, even in small amounts. The ability to carry out the alcoholysis reaction in the presence of a phosphorus-containing flame retardant, such as bisphenol A bis(diphenyl phosphate) (BPADP), is key to enabling the recycling of low-value polycarbonates since these polycarbonates can contain significant amounts of flame retardants. The process of the disclosure thus allows the efficient recycling of low-value polycarbonates by employing specific transesterification catalysts having non-neutralizable groups.

As used herein, a "polycarbonate" means compositions having repeating structural carbonate units of formula (1)

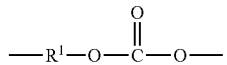

(1)

in which at least 60 percent of the total number of $R^1$ groups contain aromatic moieties and the balance thereof are aliphatic, alicyclic, or aromatic. In an embodiment, each $R^1$ is a $C_{6-30}$ aromatic group, that is, contains at least one aromatic moiety. $R^1$ can be derived from a dihydroxy compound of the formula HO—$R^1$—OH, in particular of formula (2)

$$HO-A^1-Y^1-A^2-OH \quad (2)$$

wherein each of $A^1$ and $A^2$ is a monocyclic divalent aromatic group and $Y^1$ is a single bond or a bridging group having one or more atoms that separate $A^1$ from $A^2$. In an embodiment, one atom separates $A^1$ from $A^2$. Specifically, each $R^1$ can be derived from a dihydroxy aromatic compound of formula (3)

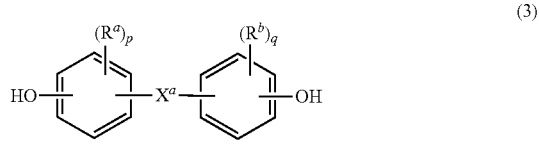

(3)

wherein $R^a$ and $R^b$ are each independently a halogen, $C_{1-12}$ alkoxy, or $C_{1-12}$ alkyl; and p and q are each independently integers of 0 to 4. It will be understood that $R^a$ is hydrogen when p is 0, and likewise $R^b$ is hydrogen when q is 0. Also in formula (3), $X^a$ is a bridging group connecting the two hydroxy-substituted aromatic groups, where the bridging group and the hydroxy substituent of each $C_6$ arylene group are disposed ortho, meta, or para (specifically para) to each other on the $C_6$ arylene group. In an embodiment, the bridging group $X^a$ is single bond, —O—, —S—, —S(O)—, —S(O)$_2$—, —C(O)—, or a $C_{1-18}$ organic group. The $C_{1-18}$ organic bridging group can be cyclic or acyclic, aromatic or non-aromatic, and can further comprise heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic bridging group. In an embodiment, p and q is each 1, and $R^a$ and $R^b$ are each a $C_{1-3}$ alkyl group, specifically methyl, disposed meta to the hydroxy group on each arylene group.

In an embodiment, $X^a$ is a substituted or unsubstituted $C_{3-18}$ cycloalkylidene, a $C_{1-25}$ alkylidene of formula —C($R^c$)($R^d$)— wherein $R^c$ and $R^d$ are each independently hydrogen, $C_{1-12}$ alkyl, $C_{1-12}$ cycloalkyl, $C_{7-12}$ arylalkyl, $C_{1-12}$ heteroalkyl, or cyclic $C_{7-12}$ heteroarylalkyl, or a group of the formula —C(=$R^e$)— wherein $R^e$ is a divalent $C_{1-12}$ hydrocarbon group. Groups of this type include methylene, cyclohexylmethylene, ethylidene, neopentylidene, and isopropylidene, as well as 2-[2.2.1]-bicycloheptylidene, cyclohexylidene, cyclopentylidene, cyclododecylidene, and adamantylidene.

In another embodiment, $X^a$ is a $C_{1-18}$ alkylene group, a $C_{3-18}$ cycloalkylene group, a fused $C_{6-18}$ cycloalkylene group, or a group of the formula —$B^1$-G-$B^2$— wherein $B^1$ and $B^2$ are the same or different $C_{1-6}$ alkylene group and G is a $C_{3-12}$ cycloalkylidene group or a $C_{6-16}$ arylene group. For example, $X^a$ can be a substituted $C_{3-18}$ cycloalkylidene of formula (4)

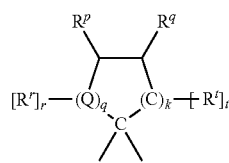

(4)

wherein $R^r$, $R^p$, $R^q$, and $R^t$ are each independently hydrogen, halogen, oxygen, or $C_{1-12}$ hydrocarbon groups; Q is a direct bond, a carbon, or a divalent oxygen, sulfur, or —N(Z)— where Z is hydrogen, halogen, hydroxy, $C_{1-12}$ alkyl, $C_{1-12}$ alkoxy, or $C_{1-12}$ acyl; r is 0 to 2, t is 1 or 2, q is 0 or 1, and k is 0 to 3, with the proviso that at least two of $R^r$, $R^p$, $R^q$, and $R^t$ taken together are a fused cycloaliphatic, aromatic, or heteroaromatic ring. It will be understood that where the fused ring is aromatic, the ring as shown in formula (4) will have an unsaturated carbon-carbon linkage where the ring is fused. When k is 1 and i is 0, the ring as shown in formula (4) contains 4 carbon atoms, when k is 2, the ring as shown in formula (4) contains 5 carbon atoms, and when k is 3, the ring contains 6 carbon atoms. In an embodiment, two adjacent groups (e.g., $R^q$ and $R^t$ taken together) form an aromatic group, and in another embodiment, $R^q$ and $R^t$ taken together form one aromatic group and $R^r$ and $R^p$ taken together form a second aromatic group. When $R^q$ and $R^t$ taken together form an aromatic group, $R^p$ can be a double-bonded oxygen atom, i.e., a ketone.

"Polycarbonates" includes homopolycarbonates (wherein each $R^1$ in the polymer is the same), copolymers comprising different $R^1$ moieties in the carbonate ("copolycarbonates"), copolymers comprising carbonate units and other types of polymer units, such as ester units, and combinations comprising at least one of homopolycarbonates or copolycarbonates.

Polycarbonates containing flame retardants are also referred to as "FR polycarbonates" herein. FR polycarbonates are used in various components and housings in electronic devices. Once the devices are discarded, plastics are separated from metal and glass components and are processed to provide potential feedstocks for industrial use. These feedstocks are referred to as plastics from e-waste. Examples of FR polycarbonate-containing e-waste include plastics from float sink e-waste and trommel e-waste.

"Float-sink e-waste" plastics are obtained via a liquid separation process. After being ground, e-waste materials are separated according to their relative buoyancy in selected liquids in a float sink tank. For example, in such processed a first float/sink tank is filled with plain water. Polyethylene and polypropylene float, and are removed from polystyrene, acrylonitrile-butadiene-styrene (ABS), and FR polycarbonate, which sink. These "sinks" go into a second tank containing an aqueous solution of 1.035 g/cc density, as well as three rotating drums with paddle vanes. Polystyrene floats in this tank, while ABS and FR polycarbonate sink. The FR polycarbonate and ABS are a compatible blend, which processors sell as float sink e-waste plastics. Float sink e-waste plastics can be obtained, for example, from Global Electric and Electronic Processing (GEEP).

Trommel e-waste plastics are plastics from e-waste that have been ground and physically sorted via trommel screening. Trommel e-waste plastics are available, for example, from Global Electric and Electronic Processing (GEEP).

E-waste materials that are first separated by hand prior to size reduction. Those parts are believed to be primarily polycarbonate/ABS blends are then hand-picked and used as recycling feedstocks. Such e-waste plastics are available from Recycletronics.

The phosphorus-containing flame retardants in the polycarbonate-containing compositions include organic phosphates and organic compounds containing phosphorus-nitrogen bonds.

One type of organic phosphate is an aromatic phosphate of the formula (GO)$_3$P=O, wherein each G is independently an alkyl, cycloalkyl, aryl, alkylaryl, or aralkyl group, provided that at least one G is an aromatic group. Two of the G groups can be joined together to provide a cyclic group, for example, diphenyl pentaerythritol diphosphite. Aromatic phosphates include, phenyl bis(dodecyl)phosphate, phenyl bis(neopentyl)phosphate, phenyl bis(3,5,5'-trimethylhexyl) phosphate, ethyl diphenyl phosphate, 2-ethylhexyl di(p-tolyl)phosphate, bis(2-ethylhexyl)p-tolyl phosphate, tritolyl phosphate, bis(2-ethylhexyl)phenyl phosphate, tri(nonylphenyl)phosphate, bis(dodecyl)p-tolyl phosphate, dibutyl phenyl phosphate, 2-chloroethyl diphenyl phosphate, p-tolyl bis(2,5,5'-trimethylhexyl)phosphate, 2-ethylhexyl diphenyl phosphate, or the like. A specific aromatic phosphate is one in which each G is aromatic, for example, triphenyl phosphate, tricresyl phosphate, isopropylated triphenyl phosphate, and the like.

Di- or polyfunctional aromatic phosphorus-containing compounds are also useful, for example, compounds of the formulae below:

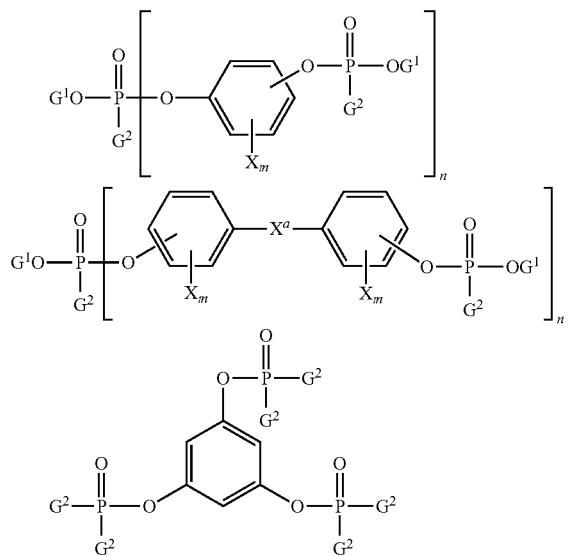

wherein each $G^1$ is independently a hydrocarbon having 1 to 30 carbon atoms; each $G^2$ is independently a hydrocarbon or hydrocarbonoxy having 1 to 30 carbon atoms; each X is independently a bromine or chlorine; m is 0 to 4, and n is 1 to 30. Di- or polyfunctional aromatic phosphorus-containing compounds include resorcinol tetraphenyl diphosphate (RDP), the bis(diphenyl)phosphate of hydroquinone and the bis(diphenyl)phosphate of bisphenol A, respectively, their oligomeric and polymeric counterparts, and the like.

Exemplary flame retardant compounds containing phosphorus-nitrogen bonds include phosphonitrilic chloride, phosphorus ester amides, phosphoric acid amides, phosphonic acid amides, phosphinic acid amides, tris(aziridinyl) phosphine oxide. The organic phosphorus-containing flame retardants are generally present in amounts of about 0.1 to about 20 parts by weight, for example, about 2 to about 18 parts by weight or about 4 to about 16 parts by weight, optionally about 2 to about 15 parts by weight, based on 100 parts by weight of the total composition, exclusive of any filler.

Polycarbonates in the FR polycarbonate compositions can be depolymerized by alcoholysis. As used herein, alcoholysis refers to a process that depolymerizes polycarbonate to produce dihydroxy aromatic compounds and dialkyl carbonates by using an alcohol as both a solvent and a reactant.

The alcohol can be a $C_{1-10}$ alcohol, for example, an alkyl alcohol such as methanol, ethanol, propanol, butanol, and an aryl alcohol such as phenol, cresols, and the like. Alcoholysis in the presence of an alkyl alcohol produces a dialkyl carbonate. Alcoholysis in the presence of an aryl alcohol produces a diaryl carbonate. Where the discussion and the examples herein refer to dialkyl carbonate, it is appreciated that the alcoholysis to recover diaryl carbonate and the use of the recovered diaryl carbonate to produce polycarbonate is also within the scope of the disclosure. When methanol is used, the alcoholysis is referred to as methanolysis, when ethanol is used, the process is referred to as ethanolyis, and so forth. Where the discussion and the examples herein refer to methanolysis, the skilled artisan will understand that other alcohols can be interchangeably used for what would generally be referred to as alcoholysis and that the latter is within the scope of the invention.

The use of a transesterification catalyst having non-neutralizable groups allows for complete depolymerization of polycarbonate in the presence of a flame retardant, even when a small amount of catalyst is used. As used herein, the term "non-neutralizable groups" refers to groups that do not react with either acids or bases. The term "transesterification catalyst having non-neutralizable groups" means a transesterification catalyst that does not contain any group that reacts with either an acid or a base.

Exemplary transesterification catalysts having non-neutralizable groups can be one or more of titanium isopropoxide (also referred to as "tetra(isopropyl)titanate" and "TPT"), an alkali metal salt, an alkaline earth metal salt, a quaternary ammonium salt of boron hydride, a quaternary ammonium salt of aluminum hydride, a hydride of an alkali metal, a hydride of an alkaline earth metal, an aryloxide of an alkali metal, an aryloxide of an alkaline earth metal, an organic salt of an alkali metal, an organic salt of an alkaline earth metal, a boron compound, a silicon compound, a germanium compound, a tin compound, an organotin compound, a lead compound, an onium compound, an antimony compound, a manganese compound, a titanium compound, a zinc compound or a zirconium compound.

The quaternary ammonium salts of boron hydride and of aluminum hydride can be lithium aluminum hydride, sodium boron hydride and tetramethyl ammonium boron hydride. The hydrides of an alkali metal and of an alkaline earth metal can be lithium hydride, sodium hydride or calcium hydride. The alkoxides of an alkali metal and of an alkaline earth metal can be lithium methoxide, sodium ethoxide, or calcium methoxide. The aryloxides of an alkali metal and of an alkaline earth metal can be lithium phenoxide, sodium phenoxide, magnesium phenoxide, LiO—Ar—OLi, wherein Ar represents an arylene group, and NaO—Ar—ONa, wherein Ar represents an arylene group. The organic salts of an alkali metal and of an alkaline earth metal can be lithium acetate, calcium acetate, or sodium benzoate. The zinc compounds can be zinc oxide, or zinc phenoxide. The boron compounds can be boron oxide, boric acid, sodium borate, trimethyl borate, tributyl borate, triphenyl borate, ammonium borate, or phosphonium borate. The silicon compounds can be silicon oxide, sodium silicate, tetraalkylsilicon, tetraarylsilicon, or diphenyl-ethyl-ethoxysilicon. The germanium compounds can be germanium oxide, germanium tetrachloride, and germanium ethnocide or germanium phenoxide. The tin compounds can be tin oxide, dialkyltin oxide, dibutyltin oxide, dialkyltin carboxylate, or tin acetate. The tin compounds that have an alkoxy group or an aryloxy group bonded to tin can include ethyltin tributoxide and organotin compounds. Lead compounds include lead oxide, lead acetate, lead carbonate, and basic lead carbonate. Alkoxides and aryloxides of lead, for example lead diphenoxide or organolead, can also be used as a metal transesterification catalyst. One example of an aryloxide of lead is lead diphenoxide. Onium compounds can include quaternary ammonium salt, quaternary phosphonium salt, or a quaternary arsonium salt. The antimony compounds can include antimony oxide and antimony acetate. The manganese compounds can include manganese acetate, manganese carbonate and manganese borate. The titanium compounds include titanium oxide and titanium alkoxides and titanium aryloxide. The zirconium compounds include zirconium acetate, zirconium oxide, zirconium alkoxide, zirconium aryloxide, and zirconium acetylacetonate.

In addition to the foregoing, transesterification catalysts used herein can include tetrabutylammonium acetate, tetrabutylphosphonium acetate, or tetrabutylphosphonium phenolate. The transesterification catalyst as used herein can be one or more of the foregoing compounds. In some embodiments, the catalyst is a tin compound, a zinc compound, a titanium compound, an aluminum compound, or a combination comprising at least one of the foregoing. In specific embodiments, the catalyst is titanium tetra(isopropyl)titanate, titanate-phosphate complex, aluminum isopropoxide, dibutyltin oxide, metal phenoxides, or a combination comprising at least one of the foregoing. Advantageously, the catalyst is a catalyst purge stream from a diphenyl carbonate production unit.

When the catalyst is a titanium-based catalyst, the catalyst can be removed by adding a sufficient amount of water to a blend of dihydroxy aromatic compound, the dialkyl compound and the alcohol to convert the catalyst to titanium dioxide, which can subsequently be filtered off.

A catalytically active amount of the catalyst can be less than 4 wt. %, 3 wt. %, 2 wt. %, 1 wt. %, 0.5 wt. %, 0.25 wt. %, 0.1 wt. %, 0.05 wt. %, 0.025 wt. %, 0.01 wt. % based on the total weight of the FR polycarbonate and the alcohol. In specific embodiments, the catalyst can be present in an amount of 0.01 wt. % to 2 wt. %, 0.01 wt. % to 1 wt. %, or 0.01 wt. % to 0.1 wt. % based upon the total weight of the FR polycarbonate and the alcohol.

The alcoholysis of polycarbonate is generally conducted at a temperature of at least 30° C., specifically a temperature from 70° C. to 200° C., more specifically 100° to 180° C., most specifically 130 to 170° C. At temperatures below 30° C., reaction rates can be too slow for economical operation. Atmospheric or super-atmospheric pressures can be used, for example up to 40 bar, specifically from 50 mbar to 40 bars, more specifically from 5 bar to 20 bar autogenesis pressure.

The alcoholysis of polycarbonate can be conducted for about 0.5 to about 10 hours, specifically about 1 to about 5 hours, more specifically about 2 to about 4 hours depending on the temperature and pressure and the specific polycarbonate-containing composition and catalyst used. Advantageously, the conversion of the polycarbonate is 99% complete in less than 4 hours.

A weight ratio of alcohol to polycarbonate-containing composition of 1:1 to 10:1, specifically 2:1 to 8:1, more specifically 2:1 to 6:1 can be used. A molar ratio of alcohol, for example, methanol, ethanol, or butanol to polycarbonate-containing composition can be 8:1 to 80:1, specifically 16:1 to 64:1, more specifically 16:1 to 48:1. While other ratios than those set out herein can be used, a slight excess of alcohol can be desirable as it is used both as a reagent and a solvent.

The alcoholysis produces dihydroxy aromatic compounds and dialkyl carbonates. Acrylonitrile-butadiene-styrene (ABS), if present in the reaction mixture, can be separated from the alcohol solution of the dihydroxy aromatic compounds and the dialkyl carbonates since ABS does not dissolve in methanol.

The combination of the alcohol and the dialkyl carbonate can be separated from the dihydroxy aromatic compound by distillation. The alcohol/dialkyl carbonate stream, which contains up to 50 wt. % of dialkyl carbonate, can be reused for alcoholysis of polycarbonates. Alternatively, the alcohol/dialkyl carbonate mixture can be separated into an alcohol rich substream and a dialkyl carbonate rich substream with each substream containing greater than 75% of alcohol or dialkyl carbonate. The alcohol rich substream can be reused to depolymerize polycarbonates. In an embodiment, one or both of the substreams are further purified prior to being used in further reactions.

Illustrative examples of dialkyl carbonates include dimethyl carbonate, diethyl carbonate, and dibutyl carbonate. Some illustrative examples of specific dihydroxy aromatic compounds include the following: 4,4'-dihydroxybiphenyl, 1,6-dihydroxynaphthalene, 2,6-dihydroxynaphthalene, bis(4-hydroxyphenyl)methane, bis(4-hydroxyphenyl)diphenylmethane, bis(4-hydroxyphenyl)-1-naphthylmethane, 1,2-bis(4-hydroxyphenyl)ethane, 1,1-bis(4-hydroxyphenyl)-1-phenylethane, 2-(4-hydroxyphenyl)-2-(3-hydroxyphenyl)propane, bis(4-hydroxyphenyl)phenylmethane, 2,2-bis(4-hydroxy-3-bromophenyl)propane, 1,1-bis(hydroxyphenyl)cyclopentane, 1,1-bis(4-hydroxyphenyl)cyclohexane, 1,1-bis(4-hydroxyphenyl)isobutene, 1,1-bis(4-hydroxyphenyl)cyclododecane, trans-2,3-bis(4-hydroxyphenyl)-2-butene, 2,2-bis(4-hydroxyphenyl)adamantane, alpha,alpha'-bis(4-hydroxyphenyl)toluene, bis(4-hydroxyphenyl)acetonitrile, 2,2-bis(3-methyl-4-hydroxyphenyl)propane, 2,2-bis(3-ethyl-4-hydroxyphenyl)propane, 2,2-bis(3-n-propyl-4-hydroxyphenyl)propane, 2,2-bis(3-isopropyl-4-hydroxyphenyl)propane, 2,2-bis(3-sec-butyl-4-hydroxyphenyl)propane, 2,2-bis(3-t-butyl-4-hydroxyphenyl)propane, 2,2-bis(3-cyclohexyl-4-hydroxyphenyl)propane, 2,2-bis(3-allyl-4-hydroxyphenyl)propane, 2,2-bis(3-methoxy-4-hydroxyphenyl)propane, 2,2-bis(4-hydroxyphenyl)hexafluoropropane, 1,1-dichloro-2,2-bis(4-hydroxyphenyl)ethylene, 1,1-dibromo-2,2-bis(4-hydroxyphenyl)ethylene, 1,1-dichloro-2,2-bis(5-phenoxy-4-hydroxyphenyl)ethylene, 4,4'-dihydroxybenzophenone, 3,3-bis(4-hydroxyphenyl)-2-butanone, 1,6-bis(4-hydroxyphenyl)-1,6-hexanedione, ethylene glycol bis(4-hydroxyphenyl)ether, bis(4-hydroxyphenyl)ether, bis(4-hydroxyphenyl)sulfide, bis(4-hydroxyphenyl)sulfoxide, bis(4-hydroxyphenyl)sulfone, 9,9-bis(4-hydroxyphenyl)fluorine, 2,7-dihydroxypyrene, 6,6'-dihydroxy-3,3,3',3'-tetramethylspiro(bis)indane ("spirobiindane bisphenol"), 3,3-bis(4-hydroxyphenyl)phthalimide, 2,6-dihydroxydibenzo-p-dioxin, 2,6-dihydroxythianthrene, 2,7-dihydroxyphenoxathin, 2,7-dihydroxy-9,10-dimethylphenazine, 3,6-dihydroxydibenzofuran, 3,6-dihydroxydibenzothiophene, and 2,7-dihydroxycarbazole, resorcinol, substituted resorcinol compounds such as 5-methyl resorcinol, 5-ethyl resorcinol, 5-propyl resorcinol, 5-butyl resorcinol, 5-t-butyl resorcinol, 5-phenyl resorcinol, 5-cumyl resorcinol, 2,4,5,6-tetrafluoro resorcinol, 2,4,5,6-tetrabromo resorcinol, or the like; catechol; hydroquinone; substituted hydroquinones such as 2-methyl hydroquinone, 2-ethyl hydroquinone, 2-propyl hydroquinone, 2-butyl hydroquinone, 2-t-butyl hydroquinone, 2-phenyl hydroquinone, 2-cumyl hydroquinone, 2,3,5,6-tetramethyl hydroquinone, 2,3,5,6-tetra-t-butyl hydroquinone, 2,3,5,6-tetrafluoro hydroquinone, 2,3,5,6-tetrabromo hydroquinone, or the like, or combinations comprising at least one of the foregoing dihydroxy compounds.

Other specific examples of dihydroxy aromatic compounds include 1,1-bis(4-hydroxyphenyl)methane, 1,1-bis(4-hydroxyphenyl)ethane, 2,2-bis(4-hydroxyphenyl)propane (also referred to as "bisphenol A" or "BPA"), 2,2-bis(4-hydroxyphenyl)butane, 2,2-bis(4-hydroxyphenyl)octane, 1,1-bis(4-hydroxyphenyl)propane, 1,1-bis(4-hydroxyphenyl)n-butane, 2,2-bis(4-hydroxy-2-methylphenyl)propane, 1,1-bis(4-hydroxy-t-butylphenyl)propane, 3,3-bis(4-hydroxyphenyl)phthalimidine, 2-phenyl-3,3-bis(4-hydroxyphenyl)phthalimidine (PPPBP), 1,1-bis(4-hydroxy-3-methylphenyl)cyclohexane (DMBPC), and 1,4:3,6-dianhydro-D-sorbitol. In one specific embodiment, the dihydroxy aromatic compound derived from the alcoholysis of polycarbonate is bisphenol A.

The obtained dihydroxy aromatic compound can be sold as is or used in further reactions including polymerization to make polycarbonate. The obtained dialkyl carbonate can react with phenol to provide diphenyl carbonate. In an embodiment, the dihydroxy aromatic compound and the dialkyl carbonate can be purified before being used for further reactions.

For example, the dihydroxy aromatic compound can be used to form a polycarbonate by polymerization with a carbonyl source, i.e., a carbonate precursor. Polymerization of the dihydroxy aromatic compound to produce a polycarbonate can be by interfacial or melt polymerization methods. Although the reaction conditions for interfacial polymerization can vary, a process generally involves dissolving or dispersing a dihydroxy aromatic compound in aqueous caustic soda or potash, adding the resulting mixture to a water-immiscible solvent medium, and contacting the reactants with a carbonate precursor in the presence of a catalyst such as triethylamine or a phase transfer catalyst, under controlled pH conditions, e.g., 8 to 12. The most commonly used water immiscible solvents include methylene chloride, 1,2-dichloroethane, chlorobenzene, toluene, and the like.

Carbonate precursors include a carbonyl halide such as carbonyl bromide or carbonyl chloride, or a haloformate such as bishaloformates of a dihydric phenol (e.g., the bischloroformates of bisphenol A, hydroquinone, or the like) or a glycol (e.g., the bishaloformate of ethylene glycol, neopentyl glycol, polyethylene glycol, or the like). Combinations comprising at least one of the foregoing types of carbonate precursors can also be used. In an embodiment, an interfacial polymerization reaction to form carbonate linkages uses phosgene as a carbonate precursor, and is referred to as a phosgenation reaction.

Among the phase transfer catalysts that can be used are catalysts of the formula $(R^3)_4Q^+X$, wherein each $R^3$ is the same or different, and is a $C_{1-10}$ alkyl group; Q is a nitrogen or phosphorus atom; and X is a halogen atom or a $C_{1-8}$ alkoxy group or $C_{6-18}$ aryloxy group. Phase transfer catalysts include, for example, $[CH_3(CH_2)_3]_4NX$, $[CH_3(CH_2)_3]_4PX$, $[CH_3(CH_2)_5]_4NX$, $[CH_3(CH_2)_6]_4NX$, $[CH_3(CH_2)_4]_4NX$, $CH_3[CH_3(CH_2)_3]_3NX$, and $CH_3[CH_3(CH_2)_2]_3NX$, wherein X is $Cl^-$, $Br^-$, a $C_{1-8}$ alkoxy group or a $C_{6-18}$ aryloxy group. An effective amount of a phase transfer catalyst can be 0.1 to 10 wt. % based on the weight of bisphenol in the phosgenation mixture. In another embodiment an effective amount of phase transfer catalyst can be 0.5 to 2 wt. % based on the weight of bisphenol in the phosgenation mixture.

Branched polycarbonate blocks can be prepared by adding a branching agent during polymerization. A chain stopper (also referred to as a capping agent) can be included during polymerization. The chain stopper limits molecular weight growth rate, and so controls molecular weight in the polycarbonate.

Alternatively, melt processes can be used to make the polycarbonates. Melt polymerization may be conducted as a batch process or as a continuous process. In either case, the melt polymerization conditions used may comprise two or more distinct reaction stages, for example, a first reaction stage in which the starting dihydroxy aromatic compound and diaryl carbonate are converted into an oligomeric polycarbonate and a second reaction stage wherein the oligomeric polycarbonate formed in the first reaction stage is converted to high molecular weight polycarbonate. Such "staged" polymerization reaction conditions are especially suitable for use in continuous polymerization systems wherein the starting monomers are oligomerized in a first reaction vessel and the oligomeric polycarbonate formed therein is continuously transferred to one or more downstream reactors in which the oligomeric polycarbonate is converted to high molecular weight polycarbonate. Typically, in the oligomerization stage the oligomeric polycarbonate produced has a number average molecular weight of about 1,000 to about 7,500 Daltons. In one or more subsequent polymerization stages the number average molecular weight (Mn) of the polycarbonate is increased to between about 8,000 and about 25,000 Daltons (using polycarbonate standard).

The term "melt polymerization conditions" is understood to mean those conditions necessary to effect reaction between a dihydroxy aromatic compound and a diaryl carbonate in the presence of a transesterification catalyst. Typically, solvents are not used in the process, and the reactants dihydroxy aromatic compound and the diaryl carbonate are in a molten state. The reaction temperature can be about 100° C. to about 350° C., specifically about 180° C. to about 310° C. The pressure may be at atmospheric pressure, supra-atmospheric pressure, or a range of pressures from atmospheric pressure to about 15 torr in the initial stages of the reaction, and at a reduced pressure at later stages, for example about 0.2 to about 15 torr. The reaction time is generally about 0.1 hours to about 10 hours.

Catalysts used in the melt transesterification polymerization production of polycarbonates can include alpha or beta catalysts. Beta catalysts are typically volatile and degrade at elevated temperatures. Beta catalysts are therefore preferred for use at early low-temperature polymerization stages. Alpha catalysts are typically more thermally stable and less volatile than beta catalysts.

The alpha catalyst can comprise a source of alkali or alkaline earth ions. The sources of these ions include alkali metal hydroxides such as lithium hydroxide, sodium hydroxide, and potassium hydroxide, as well as alkaline earth hydroxides such as magnesium hydroxide and calcium hydroxide. Other possible sources of alkali and alkaline earth metal ions include the corresponding salts of carboxylic acids (such as sodium acetate) and derivatives of ethylene diamine tetraacetic acid (EDTA) (such as EDTA tetrasodium salt, and EDTA magnesium disodium salt). Other alpha transesterification catalysts include alkali or alkaline earth metal salts of a non-volatile inorganic acid such as $NaH_2PO_3$, $NaH_2PO_4$, $Na_2HPO_3$, $KH_2PO_4$, $CsH_2PO_4$, $Cs_2HPO_4$, and the like, or mixed salts of phosphoric acid, such as $NaKHPO_4$, $CsNaHPO_4$, $CsKHPO_4$, and the like. Combinations comprising at least one of any of the foregoing catalysts can be used.

Possible beta catalysts can comprise a quaternary ammonium compound, a quaternary phosphonium compound, or a combination comprising at least one of the foregoing. The quaternary ammonium compound can be a compound of the structure $(R^4)_4N^+X^-$, wherein each $R^4$ is the same or different, and is a $C_{1-20}$ alkyl group, a $C_{4-20}$ cycloalkyl group, or a $C_{4-20}$ aryl group; and $X^-$ is an organic or inorganic anion, for example a hydroxide, halide, carboxylate, sulfonate, sulfate, formate, carbonate, or bicarbonate. Examples of organic quaternary ammonium compounds include tetramethyl ammonium hydroxide, tetrabutyl ammonium hydroxide, tetramethyl ammonium acetate, tetramethyl ammonium formate, tetrabutyl ammonium acetate, and combinations comprising at least one of the foregoing. Tetramethyl ammonium hydroxide is often used. The quaternary phosphonium compound can be a compound of the structure $(R^5)_4P^+X^-$, wherein each $R^5$ is the same or different, and is a $C_{1-20}$ alkyl group, a $C_{4-20}$ cycloalkyl group, or a $C_{4-20}$ aryl group; and $X^-$ is an organic or inorganic anion, for example a hydroxide, halide, carboxylate, sulfonate, sulfate, formate, carbonate, or bicarbonate. Where $X^-$ is a polyvalent anion such as carbonate or sulfate it is understood that the positive and negative charges in the quaternary ammonium and phosphonium structures are properly balanced. For example, where $R^{20}$-$R^{23}$ are each methyl groups and $X^-$ is carbonate, it is understood that $X^-$ represents $2(CO_3^{-2})$. Examples of organic quaternary phosphonium compounds include tetramethyl phosphonium hydroxide, tetramethyl phosphonium acetate, tetramethyl phosphonium formate, tetrabutyl phosphonium hydroxide, tetrabutyl phosphonium acetate (TBPA), tetraphenyl phosphonium acetate, tetraphenyl phosphonium phenoxide, and combinations comprising at least one of the foregoing. TBPA is often used.

The amount of alpha and beta catalyst used can be based upon the total number of moles of dihydroxy compound used in the polymerization reaction. When referring to the ratio of beta catalyst, for example, a phosphonium salt, to all dihydroxy compounds used in the polymerization reaction, it is convenient to refer to moles of phosphonium salt per mole of the dihydroxy compound, meaning the number of moles of phosphonium salt divided by the sum of the moles of each individual dihydroxy compound present in the reaction mixture. The alpha catalyst can be used in an amount sufficient to provide $1\times10^{-2}$ to $1\times10^{-8}$ moles, specifically, $1\times10^{-4}$ to $1\times10^{-7}$ moles of metal per mole of the dihydroxy compounds used. The amount of beta catalyst (e.g., organic ammonium or phosphonium salts) can be $1\times10^{-2}$ to $1\times10^{-5}$, specifically $1\times10^{-3}$ to $1\times10^{-4}$ moles per total mole of the dihydroxy compounds in the reaction mixture.

Branched polycarbonate blocks can be prepared by adding a branching agent during polymerization. These branching agents include polyfunctional organic compounds containing at least three functional groups selected from hydroxyl, carboxyl, carboxylic anhydride, haloformyl, and mixtures of the foregoing functional groups. Specific examples include trimellitic acid, trimellitic anhydride, trimellitic trichloride, tris-p-hydroxy phenyl ethane, isatin-bis-phenol, tris-phenol TC (1,3,5-tris((p-hydroxyphenyl)isopropyl)benzene), tris-phenol PA (4(4(1,1-bis(p-hydroxyphenyl)-ethyl)alpha,alpha-dimethyl benzyl) phenol), 4-chloroformyl phthalic anhydride, trimesic acid, and benzophenone tetracarboxylic acid. The branching agents can be added at a level of 0.05 to 2.0 weight %. Mixtures comprising linear polycarbonates and branched polycarbonates can be used. The content of the following branching structures is 2,000 ppm or below.

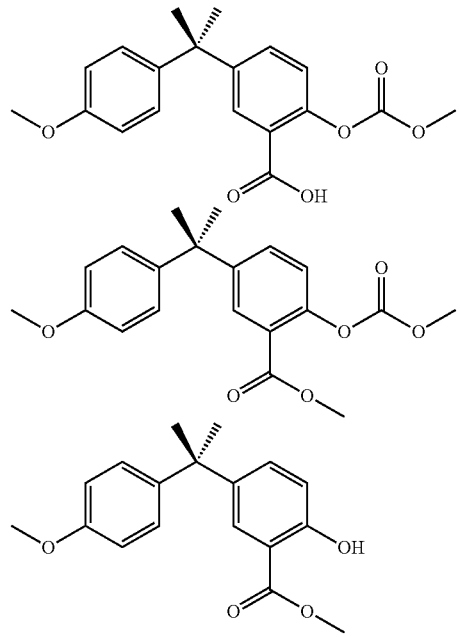

In summary, disclosed herein is are methods for recovering a dihydroxy aromatic compound and a dialkyl carbonate from a composition comprising a polycarbonate and a phosphorus-containing flame retardant, for example bisphenol A bis(diphenyl phosphate), resorcinol bis(diphenyl phosphate), or a combination thereof, optionally wherein the composition further comprises acrylonitrile-butadiene-styrene, the method including heating the polycarbonate-containing composition in the presence of an alcohol, preferably 200 weight percent to 600 weight percent of the alcohol based upon the weight of polycarbonate-containing composition, and preferably a $C_{1-10}$ alcohol such as ethanol or n-butanol, most preferably methanol, and a transesterification catalyst, preferably from 0.01 wt. % to 2 wt. %, most preferably from 0.01 to 1 wt. %, of the catalyst based upon the total weight of the polycarbonate-containing composition, and the alcohol, the catalyst having non-neutralizable groups, preferably wherein the catalyst is a tin compound, a zinc compound, a titanium compound, an aluminum compound, or a combination comprising at least one of the foregoing, most preferably wherein the catalyst is tetra (isopropyl)titanate, titanate-phosphate complex, dibutyltin oxide, aluminum isopropoxide, a metal phenoxide, or a combination comprising at least one of the foregoing, at a temperature of 70° C. to 200° C. and a pressure of 50 mbar to 40 bar for a time sufficient to depolymerize the polycarbonate to provide a dihydroxy aromatic compound and a dialkyl carbonate, preferably wherein the polycarbonate is bisphenol A polycarbonate, the dihydroxy aromatic compound is bisphenol-A, and the dialkyl carbonate is dimethyl carbonate (or is diethyl carbonate or dibutyl carbonate); and optionally further including one or more of: separating the dihydroxy aromatic compound and the dialkyl carbonate from acrylonitrile-butadiene-styrene by filtration; separating a blend of the alcohol and the dialkyl carbonate from the dihydroxy aromatic compound by distillation; when the catalyst is a titanium-based catalyst, removing the catalyst by adding a sufficient amount of water to a blend of dihydroxy aromatic compound, the dialkyl compound and the alcohol to convert the catalyst to titanium dioxide and filtering to remove titanium dioxide. A method for the manufacture of a polycarbonate includes polymerizing the recovered dihydroxy aromatic compound of any of the foregoing embodiments and a carbonyl source to provide the polycarbonate. Another method for the manufacture of a polycarbonate, the method includes recovering the dihydroxy aromatic compound and the dialkyl carbonate of any of the foregoing embodiments; reacting the recovered dialkyl carbonate with phenol to provide diphenyl carbonate; and polymerizing the recovered dihydroxy aromatic compound and diphenyl carbonate to provide the polycarbonate. A polycarbonate manufactured by either of the foregoing methods is also described. A method for the manufacture of diphenyl carbonate includes recovering the dialkyl carbonate of any of the foregoing embodiments, and reacting the recovered dialkyl carbonate with phenol to provide diphenyl carbonate.

The various embodiments are further illustrated by the following non-limiting examples.

EXAMPLES

The materials used in the Examples or produced by the processes of the Examples are described in Table 1.

TABLE 1

| Component | Description | Source |
| --- | --- | --- |
| Polycarbonate Feedstock #1 | A polycarbonate feedstock containing about 70 wt. % of bisphenol A polycarbonate; about 17 wt. % of acrylonitrile-butadiene-styrene; and about 11 wt. % of bisphenol A bis(diphenyl phosphate). | SABIC |
| Polycarbonate Feedstock #2 (Recycle Grade-E-waste) | Polymer blends recovered from electronic devices containing about 70 wt. % of polycarbonates as determined by IR | Recycletronics |
| Polycarbonate Feedstock #3 (Recycle Grade-Trommel e-waste) | E-waste that has been ground and physically sorted via trommel screening containing about 10 wt. % of polycarbonates as determined by IR | Global Electric and Electronic Processing |
| Al-isopropoxide | Aluminum isopropoxide | Sigma Aldrich |
| Dibutyltin oxide | | Sigma Aldrich |
| Zn acetate | Zinc acetate | Sigma Aldrich |
| Titanium - isopropoxide (TPT) | Tetra(isopropyl) titanate | Sigma Aldrich |
| TMAH | Tetramethylammonium hydroxide | Sigma Aldrich |
| Phosphoric acid | | Sigma Aldrich |
| Methanol | | Merck |
| BPA | 2,2-Bis(4-hydroxyphenyl) propane | Alcoholysis product |
| DMC | Dimethyl carbonate | Alcoholysis product |

Example 1

The example illustrates the methanolysis of polycarbonate feedstock #1 with TPT catalyst in the presence of phosphoric acid.

Methanolysis studies were conducted in a 2-liter (titanium) Amar High Pressure Reactor equipped with a heating jacket with a jacket oil heater and a cooling coil with a cooling water tank. The reactor was also equipped with a bottom discharge valve for removal of the reaction mass. The reactor was flushed several times with pressurized nitrogen, prior to commencement of each experiment, thereby ensuring an oxygen-free atmosphere inside the reactor. The reactor was charged with 100 g of polycarbonate feedstock #1, 600 g of methanol and 266 mg (0.04 wt. %) of TPT catalyst, along with 65 mg of phosphoric acid (TPT:phosphoric acid ratio=1:0.6). The reactor was again flushed several times with pressurized nitrogen. This also ensured zero leak conditions of the system. The speed of agitation was then adjusted to the desired value. The reactor contents were heated to 150° C. by circulating hot oil through the reactor jacket with an autogenesis pressure of 13 bar. The temperature of the reactor was controlled within ±0.5° C. of the set temperature by circulating cold water through the cooling coil. Once the desired temperature was reached, the time was noted as time zero. The entire system was thus operated in a batch mode for 180 minutes. At the end of the experiment, the reactor contents were cooled to 25-30° C. by circulating cooling water through the cooling coil. The reactor was then depressurized to atmospheric pressure manually by opening the vent valve and the reactor contents were drained via the bottom discharge valve. The reaction mixture containing BPA, methanol, and DMC was filtered and the insoluble separated. The filtrate was distilled to remove methanol and DMC. Solid BPA left behind was analyzed for purity by High Performance Liquid Chromatography (HPLC). DMC was analyzed by Gas Chromatography (GC). The results for Example 1 are shown in Table 2.

Example 2

The example illustrates the methanolysis of polycarbonate feedstock #1 with aluminum isopropoxide catalyst.

Example 1 was repeated except that 0.05 wt. % Al-isopropoxide catalyst was used in place of TPT and phosphoric acid. The process and conditions were otherwise identical to those described in Example 1. Results for Example 2 are shown in Table 2.

Example 3

The example illustrates the methanolysis of polycarbonate feedstock #1 with dibutyl tin oxide catalyst.

Example 1 was repeated except that 0.01 wt. % dibutyltin oxide catalyst was used in place of TPT and phosphoric acid. The process and conditions were otherwise identical to those described in Example 1. Results for Example 3 are shown in Table 2.

Example 4

The example illustrates the methanolysis of polycarbonate feedstock #1 with TPT catalyst.

Example 1 was repeated except that 0.04 wt. % TPT catalyst was used in place of TPT and phosphoric acid. The process steps and conditions were otherwise identical to those described in Example 1. The results from Example 4 are listed in Table 2.

Example 5

Example 1 was repeated except that no phosphoric acid was present and the quantity of methanol was three times instead of six times of the quantity of the polycarbonate feedstock #1. The process and conditions were otherwise identical to those described in Example 1. Results for Example 5 are shown in Table 2.

Example 6

Example 1 was repeated except that no phosphoric acid was present and the quantity of methanol was two times instead of six times of the quantity of the polycarbonate feedstock #1. The process and conditions were otherwise identical to those described in Example 1. Results for Example 6 are shown in Table 2.

Example 7

The example illustrates the methanolysis of commercial plastics from electronic waste containing 70% polycarbonate (polycarbonate feedstock #2) with TPT catalyst.

Example 1 was repeated except that no phosphoric acid was present and the polycarbonate feedstock #2 was used in place of polycarbonate feedstock #1, and TPT was used rather than the combination of TPT and phosphoric acid. The process and conditions were otherwise identical to those described in Example 1. Results for Example 7 are shown in Table 2.

Example 8

The example illustrates the methanolysis of commercial plastics from electronic waste containing 10% polycarbonate (polycarbonate feedstock #3) with TPT catalyst.

Example 1 was repeated except that no phosphoric acid was present and the polycarbonate feedstock #3 was used in place of polycarbonate feedstock #1, and TPT was used. The process and conditions were otherwise identical to those described in Example 1. Results for Example 8 are shown in Table 2.

Comparative Example A

The example illustrates the methanolysis of polycarbonate feedstock #1 with zinc acetate catalyst.

Example 1 was repeated except that 0.02 wt. % zinc acetate catalyst was used in place of TPT and no phosphoric acid was present. The process and conditions were otherwise identical to those described in Example 1. Results for Comparative Example A are shown in Table 2.

Comparative Example B

The examples illustrate the methanolysis of polycarbonate feedstock #1 with tetramethylammonium hydroxide catalyst. There are four separate experiments that used this catalyst—three of which did not result in substantial conversion of polycarbonate. The one that resulted in substantial conversion of polycarbonate involved treatment of the polycarbonate-containing blend with triethylamine to neutralize any acids present in the blend.

Comparative Example B1

40 g of the polycarbonate-containing blend was added to a reactor with 80 g methanol and 1.66 g of a 40% solution of tetramethylammonium hydroxide. The reactor was closed and heated to 175° C. while stirred at 500 rpm. The reactor was held at a temperature of 175° C. and 20 bar for 60 minutes, and then cooled to room temperature. Upon opening the reactor, the solid pellets were swollen by solvent but were not completely reacted.

Comparative Example B2

72 g of polycarbonate feedstock #1 was added to 831 g of methylene chloride. The mixture was agitated for 145 minutes at room temperature to dissolve the polycarbonate. The solution was filtered to remove insoluble materials including ABS. The remaining solution was added to 1200 g of water. The temperature was increased to boil off the methylene chloride resulting in the precipitation of a solid primarily consisting of polycarbonate. This solid was filtered and dried in an oven at 100° C. to remove residual water. 40 g of this material was added to a reactor with 80 g methanol and 1.66 g of a 40% solution of Tetramethylammonium hydroxide. The reactor was closed and heated to 175° C. while stirred at 500 rpm. The reactor was held at a temperature of 175° C. and 20 bar for 60 minutes, and then cooled to room temperature. Upon opening the reactor, the solid was still present and was approximately 70.5% polycarbonate.

Comparative Example B3

72 g of polycarbonate feedstock #1 was added to 621 g of methylene chloride. The mixture was agitated for 145 minutes at room temperature to dissolve the polycarbonate. The solution was filtered to remove insoluble materials including ABS. 200 g of methanol was slowly added to the remaining solution resulting in the precipitation of a solid primarily consisting of polycarbonate. This solid was filtered and dried in an oven at 100° C. to remove residual solvent. 40 g of this material was added to a reactor with 80 g methanol and 1.66 g of a 40% solution of Tetramethylammonium hydroxide. The reactor was closed and heated to 175° C. while stirred at 500 rpm. The reactor was held at a temperature of 175° C. and 200 psi for 60 minutes, and then cooled to room temperature. Upon opening the reactor, the solid was still present. Fourier transform infrared (FTIR) analysis of the solid indicated that there was a substantial amount of polycarbonate remaining in the solid.

Comparative Example B4

42 g of polycarbonate feedstock #1 was added to 431 g of methylene chloride. The mixture was agitated for 120 minutes at room temperature to dissolve the polycarbonate. The solution was filtered to remove insoluble materials including ABS. 400 g of water and 30 g of triethylamine were added to the remaining solution. A small amount of solid was formed and filtered off. The temperature was increased to boil off the methylene chloride resulting in the precipitation of a solid primarily consisting of polycarbonate. This solid was filtered and dried in an oven at 100° C. to remove residual water. 16.1 g of this material was added to a reactor with 32.2 g methanol and 0.67 g of a 40% solution of Tetramethylammonium hydroxide. The reactor was closed and heated to 175° C. while stirred at 500 rpm. The reactor was held at a temperature of 175° C. and 20 bar for 60 minutes, and then cooled to room temperature. Upon opening the reactor, 3.1 g of solid remained, primarily consisting of ABS. The polycarbonate was substantially reacted using this process.

TABLE 2

| Ex/CEx | Polycarbonate-containing composition (wt. % of PC[3]) | Catalyst/ Loading level[1] | Methanol loading level[2] | BPA yield[3] (wt. %) | BPA purity[3] (wt. %) | DMC yield[3] (wt. %) |
|---|---|---|---|---|---|---|
| 1 | Polycarbonate Feedstock #1 (70 wt. %) | TPT/Phosphoric acid 0.04 wt. % | 6 | 83 | 78.8 | 73 |
| 2 | Polycarbonate Feedstock #1 (70 wt. %) | Al isopropoxide 0.05 wt. % | 6 | 83 | 77.5 | 74 |
| 3 | Polycarbonate Feedstock #1 (70 wt. %) | Dibutyl tin oxide 0.01 wt. % | 6 | 86 | 79.9 | 76 |
| 4 | Polycarbonate Feedstock #1 (70 wt. %) | TPT 0.04 wt. % | 6 | 84 | 80 | 76 |
| 5 | Polycarbonate Feedstock #1 (70 wt. %) | TPT 0.07 wt. % | 3 | 80 | 78.6 | 61 |
| 6 | Polycarbonate Feedstock #1 (70 wt. %) | TPT 0.09 wt. % | 2 | 81 | 79 | 68 |
| 7 | Feedstock #2 Recycle Grade (70 wt. %) | TPT 0.04 wt. % | 6 | 88 | 78.7 | 73 |
| 8 | Feedstock #3 Recycle Grade (10 wt. %) | TPT 0.04 wt. % | 6 | 90.4 | 64 | 98.2 |
| A | Polycarbonate Feedstock #1 | Zinc Acetate 0.02 wt. % | 6 | 14 | 29 | 14.1 |
| B-1 | Polycarbonate Feedstock #1 (70 wt. %) | TMAH 0.6 wt. % | 2 | No substantial conversion of polycarbonate | | |
| B-2 | Polycarbonate Feedstock #1 (70 wt. %) | TMAH 0.6 wt. % | 2 | No substantial conversion of polycarbonate | | |
| B-3 | Polycarbonate Feedstock #1 (70 wt. %) | TMAH 0.6 wt. % | 2 | No substantial conversion of polycarbonate | | |
| B-4 | Polycarbonate Feedstock #1 (70 wt. %) | TMAH/ Triethylamine 0.6 wt. % | 2 | Substantial conversion observed | | |

[1]The catalyst loading level is a weight percent based on the total weight of the feedstock.
[2]The methanol loading level is calculated by dividing the weight of methanol over the weight of the feedstock.
[3]The content of polycarbonate (PC) was determined by IR; BPA content and purity were quantified by HPLC; and DMC content was quantified by GC.

Examples 9 Through 15 and Comparative Examples C Through P

Experiments were conducted to determine the required catalyst amounts to achieve complete reaction (defined as greater than 99% PC conversion). A polycarbonate ("PC") conversion of less than 99% is considered ineffective.

Forty g of the polycarbonate feedstock #1 was added to a reactor with 80 g methanol and a catalyst shown in Table 3. The reactor was closed and heated to 175° C. while stirred at 500 rpm. The reactor was held at a temperature of 175° C. and 20 bar for 60 minutes. The reactor was then cooled to room temperature. The solid and liquid phases were analyzed for composition.

Based on the below results, it is observed that for sodium hydroxide, 1.25% catalyst loading was ineffective while 2.5% resulted in complete conversion of polycarbonate. For potassium hydroxide, 2.5% was ineffective while 5% resulted in complete conversion. For triethylamine, 0.75% was ineffective while 1.25% resulted in complete conversion. In contrast, in experiments using TPT (TPT) complete conversion was achieved at catalyst concentrations down to 0.025 wt. %.

TABLE 3

| Ex/CEx | Catalyst | % PC Conversion |
|---|---|---|
| C | TMAH (40% solution in water) - 1.66 g | 96.85% |
| D | TMAH (40% solution in water) - 1.66 g + 5 g triethylamine | 99.39% |
| E | Triethylamine 0.5 g | 99.72% |
| F | Triethylamine 0.3 g | 98.58% |
| G | Triethylamine 0.05 g | 92.09% |
| H | NaOH 0.1 g | 95.90% |
| I | NaOH 0.01 g | 91.16% |
| J | NaOH 0.01 g Repeat | 98.84% |
| K | NaOH 0.5 g | 98.73% |
| L | NaOH 1.0 g | 99.46% |
| M | KOH 0.1 g | 80.04% |
| N | KOH 0.5 g | 94.91% |
| O | KOH 1.0 g | 98.90% |
| P | KOH 2.0 g | 99.60% |
| 9 | TPT 0.8 mL | 99.76% |
| 10 | TPT 0.4 mL | 99.73% |
| 11 | TPT 0.2 mL | 99.92% |
| 12 | TPT 0.1 mL | 99.96% |
| 13 | TPT 0.05 mL | 99.49% |
| 14 | TPT 0.02 mL | 99.66% |
| 15 | TPT 0.01 mL | 99.65% |

The singular forms "a," "an," and "the" include plural referents unless the context clearly dictates otherwise. "Or" means "and/or." Thus, reference to "compositions containing flame retardant or ABS," for example, means composition containing flame retardant, ABS, or both. The endpoints of all ranges directed to the same component or property are inclusive and independently combinable. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs.

As used herein, a "combination" is inclusive of blends, mixtures, alloys, reaction products, and the like. Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

As used herein, the term "hydrocarbyl" and "hydrocarbon" refers broadly to a substituent comprising carbon and hydrogen, optionally with 1 to 3 heteroatoms, for example, oxygen, nitrogen, halogen, silicon, sulfur, or a combination thereof; "alkyl" refers to a straight or branched chain, saturated monovalent hydrocarbon group; "alkylene" refers to a straight or branched chain, saturated, divalent hydrocarbon group; "alkylidene" refers to a straight or branched chain, saturated divalent hydrocarbon group, with both valences on a single common carbon atom; "alkenyl" refers to a straight or branched chain monovalent hydrocarbon group having at least two carbons joined by a carbon-carbon double bond; "cycloalkyl" refers to a non-aromatic monovalent monocyclic or multicylic hydrocarbon group having at least three carbon atoms, "cycloalkenyl" refers to a non-aromatic cyclic divalent hydrocarbon group having at least three carbon atoms, with at least one degree of unsaturation; "aryl" refers to an aromatic monovalent group containing only carbon in the aromatic ring or rings; "arylene" refers to an aromatic divalent group containing only carbon in the aromatic ring or rings; "alkylaryl" refers to an aryl group that has been substituted with an alkyl group as defined above, with 4-methylphenyl being an exemplary alkylaryl group; "arylalkyl" refers to an alkyl group that has been substituted with an aryl group as defined above, with benzyl being an exemplary arylalkyl group; "acyl" refers to an alkyl group as defined above with the indicated number of carbon atoms attached through a carbonyl carbon bridge (—C(=O)—); "alkoxy" refers to an alkyl group as defined above with the indicated number of carbon atoms attached through an oxygen bridge (—O—); and "aryloxy" refers to an aryl group as defined above with the indicated number of carbon atoms attached through an oxygen bridge (—O—).

Unless otherwise indicated, each of the foregoing groups can be unsubstituted or substituted, provided that the substitution does not significantly adversely affect synthesis, stability, or use of the compound. The term "substituted" as used herein means that at least one hydrogen on the designated atom or group is replaced with another group, provided that the designated atom's normal valence is not exceeded. When the substituent is oxo (i.e., =O), then two hydrogens on the atom are replaced. Combinations of substituents or variables are permissible provided that the substitutions do not significantly adversely affect synthesis or use of the compound. Exemplary groups that can be present on a "substituted" position include, but are not limited to, cyano; hydroxyl; nitro; azido; alkanoyl (such as a $C_{2-6}$ alkanoyl group such as acyl); carboxamido; $C_{1-6}$ or $C_{1-3}$ alkyl, cycloalkyl, alkenyl, and alkynyl (including groups having at least one unsaturated linkages and from 2 to 8, or 2 to 6 carbon atoms); $C_{1-6}$ or $C_{1-3}$ alkoxy groups; $C_{6-10}$ aryloxy such as phenoxy; $C_{1-6}$ alkylthio; $C_{1-6}$ or $C_{1-3}$ alkylsulfinyl; $C_{1-6}$ or $C_{1-3}$ alkylsulfonyl; aminodi($C_{1-6}$ or $C_{1-3}$)alkyl; $C_{6-12}$ aryl having at least one aromatic rings (e.g., phenyl, biphenyl, naphthyl, or the like, each ring either substituted or unsubstituted aromatic); $C_{7-19}$ alkylenearyl having 1 to 3 separate or fused rings and from 6 to 18 ring carbon atoms, with benzyl being an exemplary arylalkyl group; or arylalkoxy having 1 to 3 separate or fused rings and from 6 to 18 ring carbon atoms, with benzyloxy being an exemplary arylalkoxy group.

All references cited herein are incorporated by reference in their entirety. While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

What is claimed is:

1. A method for recovering a dihydroxy aromatic compound and a dialkyl carbonate from a composition comprising a polycarbonate and a phosphorus-containing flame retardant, the method comprising
heating the polycarbonate-containing composition in the presence of an alcohol and a transesterification catalyst, having non-neutralizable groups, selected from the group consisting of a tin compound, a zinc compound, a titanium compound, an aluminum compound, or a combination thereof, at a temperature of 70° C. to 200° C. and a pressure of 50 mbar to 40 bar for a time sufficient to depolymerize the polycarbonate to provide a dihydroxy aromatic compound and a dialkyl carbonate;
wherein the catalyst is present in an amount from 0.01 wt. % to 1 wt. % based upon the total weight of the polycarbonate-containing composition and the alcohol.

2. The method of claim 1, wherein the composition further comprises acrylonitrile-butadiene-styrene.

3. The method of claim 2, wherein the method further comprises separating the dihydroxy aromatic compound and the dialkyl carbonate from acrylonitrile to butadiene-styrene by filtration.

4. The method of claim 1, further comprising separating a blend of the alcohol and the dialkyl carbonate from the dihydroxy aromatic compound by distillation.

5. The method of claim 1, wherein the polycarbonate is bisphenol A polycarbonate, the dihydroxy aromatic compound is bisphenol-A, and the dialkyl carbonate is dimethyl carbonate.

6. The method of claim 5, wherein the alcohol is a $C_{1-10}$ alcohol.

7. The method of claim 6, wherein the alcohol is methanol.

8. The method of claim 6, wherein the alcohol is ethanol or n-butanol.

9. The method of claim 8, wherein the dialkyl carbonate is diethyl carbonate or dibutyl carbonate.

10. The method of claim 1, wherein the phosphorus-containing flame retardant is bisphenol A bis(diphenyl phosphate), resorcinol bis(diphenyl phosphate), or a combination thereof.

11. The method of claim 1, wherein the catalyst is tetra(isopropyl)titanate, titanate-phosphate complex, dibutyltin oxide, aluminum isopropoxide, a metal phenoxide, or a combination comprising at least one of the foregoing.

12. The method of claim 1, wherein the catalyst is a catalyst purge stream from a diphenyl carbonate product unit.

13. The method of claim 1, wherein the catalyst is a titanium-based catalyst, and wherein the method further comprises removing the catalyst by adding a sufficient amount of water to a blend of dihydroxy aromatic compound, the dialkyl compound and the alcohol to convert the catalyst to titanium dioxide and filtering to remove titanium dioxide.

14. The method of claim 1, wherein the catalyst is present in an amount from 0.01 wt. % to 1 wt. % based upon the total weight of the polycarbonate-containing composition and the alcohol.

15. The method of claim 14, wherein the catalyst is present in an amount from 0.01 wt. % to 0.1 wt. % based upon the total weight of the polycarbonate-containing composition and the alcohol.

16. The method of claim 1, wherein the alcohol is present in an amount of 200 weight percent to 600 weight percent based upon the weight of polycarbonate-containing composition.

17. The method of claim 1, wherein the alcohol is added as a methanol stream containing from 0 to 50 weight percent dimethyl carbonate.

18. The method of claim 1, wherein the method further comprises: polymerizing the recovered dihydroxy aromatic compound and a carbonyl source to provide the polycarbonate.

19. The method of claim 1, further comprising recovering the dialkyl carbonate; and reacting the recovered dialkyl carbonate with phenol to provide diphenyl carbonate.

20. The method of claim 1, further comprising
   recovering the dihydroxy aromatic compound and the dialkyl carbonate;
   reacting the recovered dialkyl carbonate with phenol to provide diphenyl carbonate;
   polymerizing the recovered dihydroxy aromatic compound and diphenyl carbonate to provide the polycarbonate.

* * * * *